United States Patent [19]

Taylor

[11] Patent Number: 5,133,855
[45] Date of Patent: Jul. 28, 1992

[54] INTEGRAL CAP FOR ELECTRODE AND ELECTRODE EMPLOYING SAME

[75] Inventor: Dale F. Taylor, Schenectady, N.Y.
[73] Assignee: General Electric Company, Schenectady, N.Y.
[21] Appl. No.: 574,878
[22] Filed: Aug. 30, 1990
[51] Int. Cl.⁵ ............................................. G01N 27/30
[52] U.S. Cl. ..................... 204/435; 204/279; 204/286; 204/297 R; 204/400; 228/263.11; 228/263.12; 376/245; 376/256
[58] Field of Search ................... 204/286, 297 R, 400, 204/416-420, 435, 279; 376/256, 245

[56] References Cited

U.S. PATENT DOCUMENTS

| | | | |
|---|---|---|---|
| 2,190,835 | 2/1940 | Gruss et al. | 204/435 |
| 4,177,126 | 12/1979 | Imaki et al. | 204/435 |
| 4,882,029 | 11/1989 | Eickmann | 204/400 |
| 4,889,608 | 12/1989 | Eickmann | 204/435 |
| 4,948,492 | 8/1990 | Niedrach et al. | 204/435 |

Primary Examiner—T. Tung
Attorney, Agent, or Firm—James E. McGinness; James C. Davis, Jr.; James Magee, Jr.

[57] ABSTRACT

A container for electrochemical reactants for an electrode is provided, as well as electrodes employing the same. The electrodes can withstand the rigorous environment of a nuclear reactor core. The design of the container reduces stresses in the electrode and significantly improves its reliability. The container has a generally cylindrical member of an insulator. The member has a base region with a cut-out extending therethrough. Sidewall means extend from the base to define a cavity for containing electrochemical reactants, e.g., silver chloride. An insert of an insulator at one end mates with the cut-out and at another end mates with and is brazed to a cap for the container. The insert has a second sidewall means for holding the electrochemical reactants, and is shaped to fit within the first sidewall means. The base of the insert and the the cut-out are metallized for acceptance of a silver base. The design of the container and insert obviate the need for a wire to hold down the cap, thus overcoming problems of previous electrodes.

24 Claims, 3 Drawing Sheets

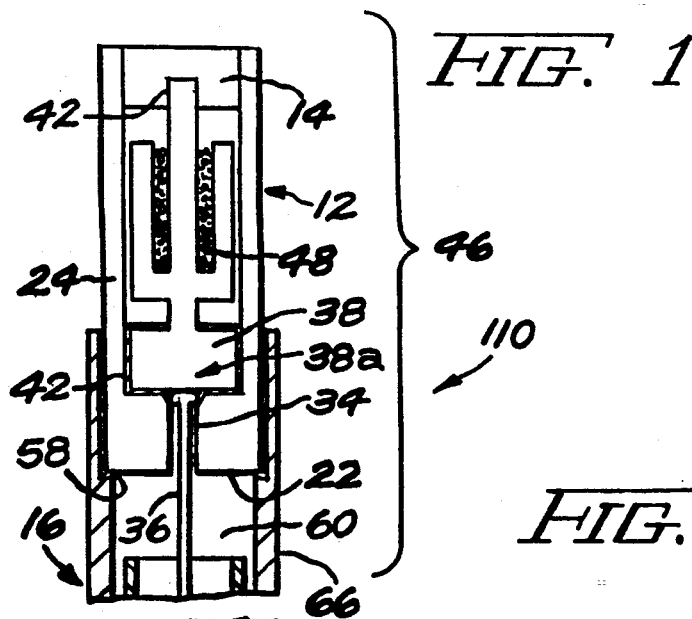
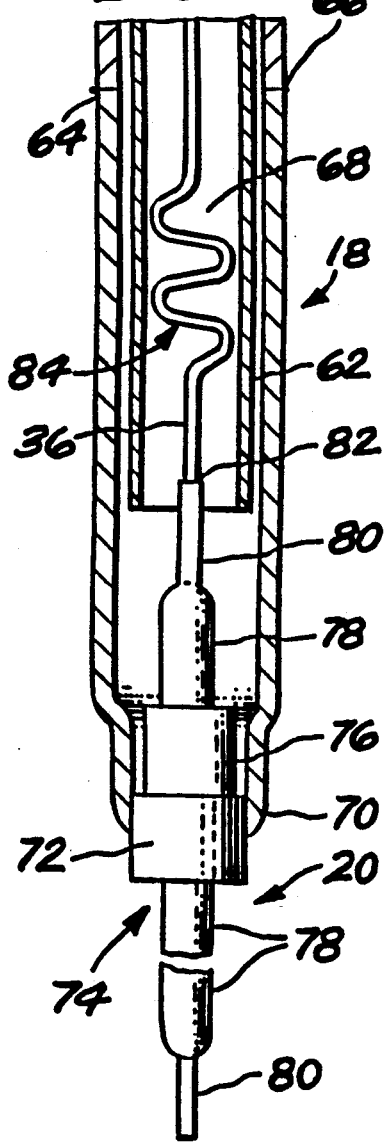
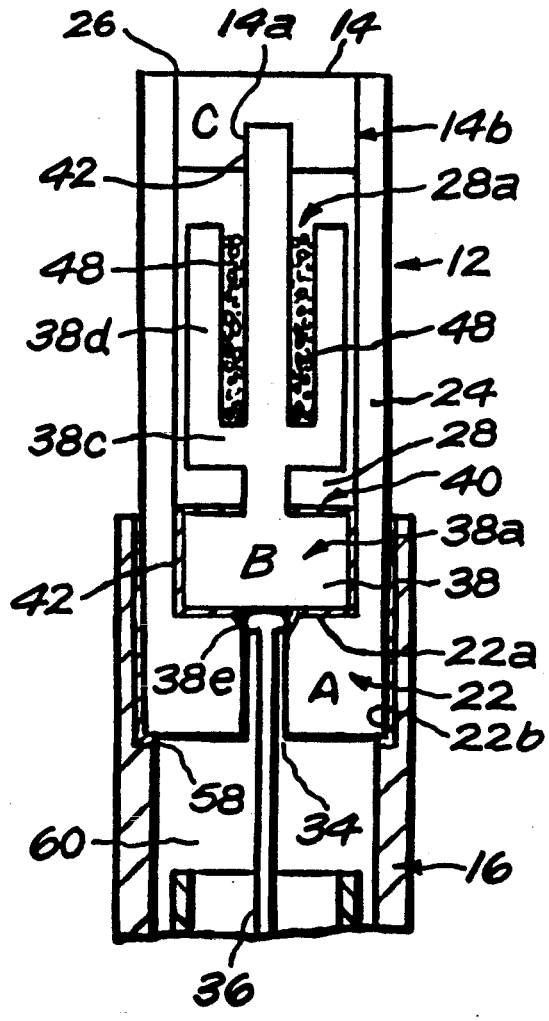
FIG. 1
FIG. 2

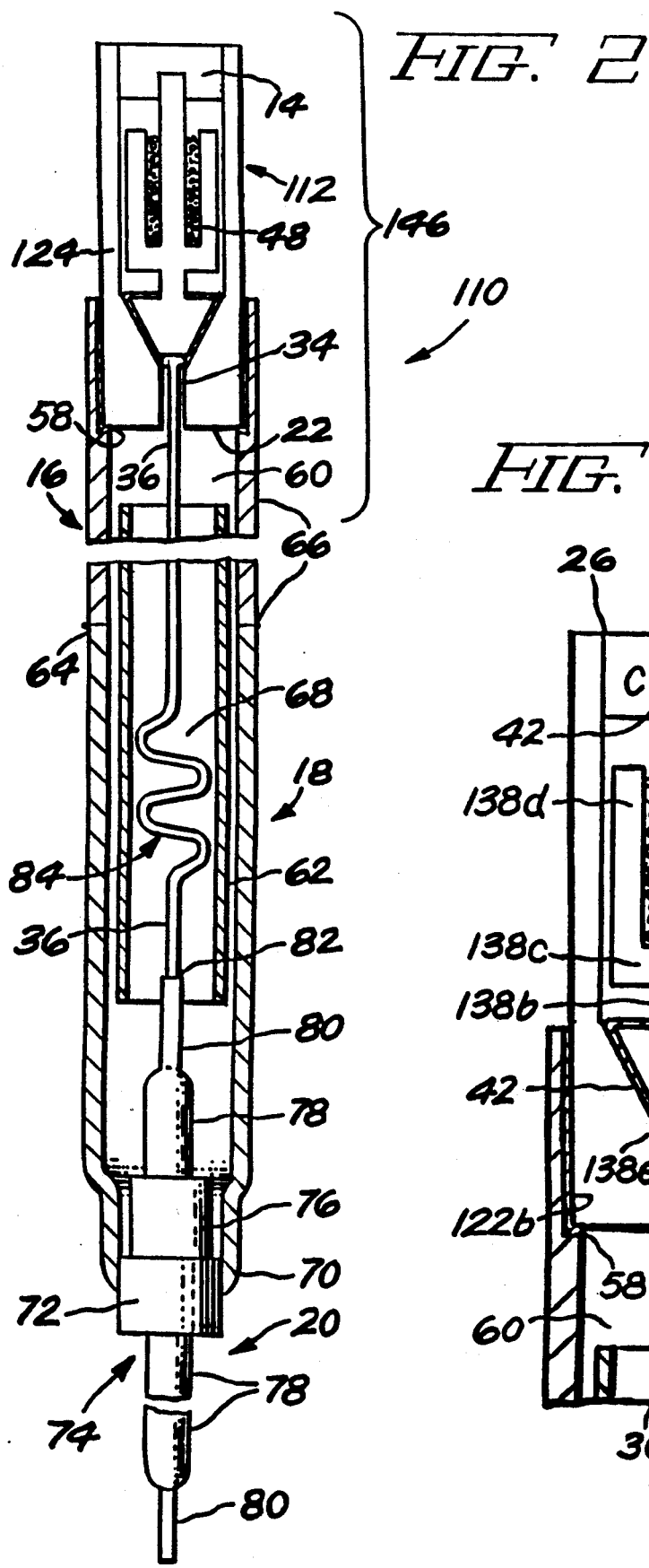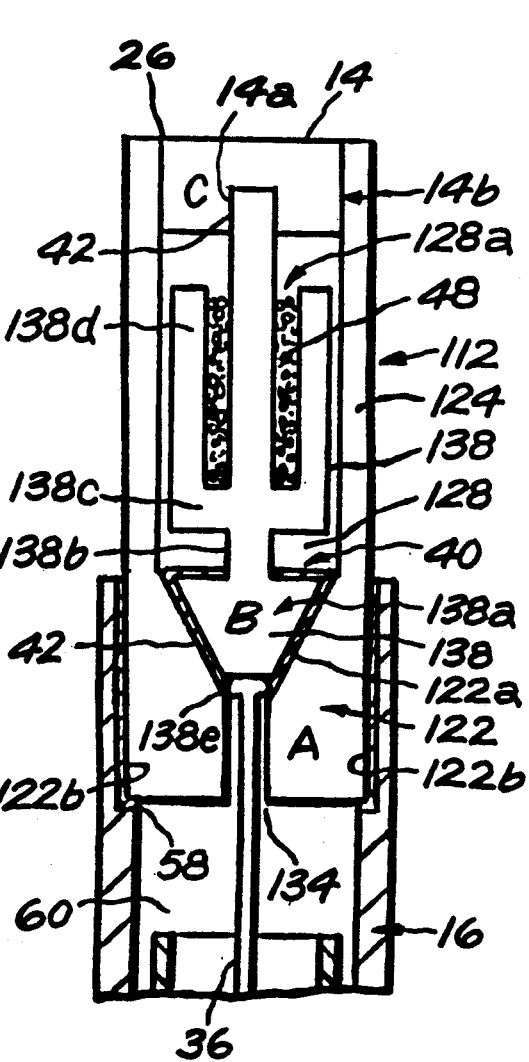

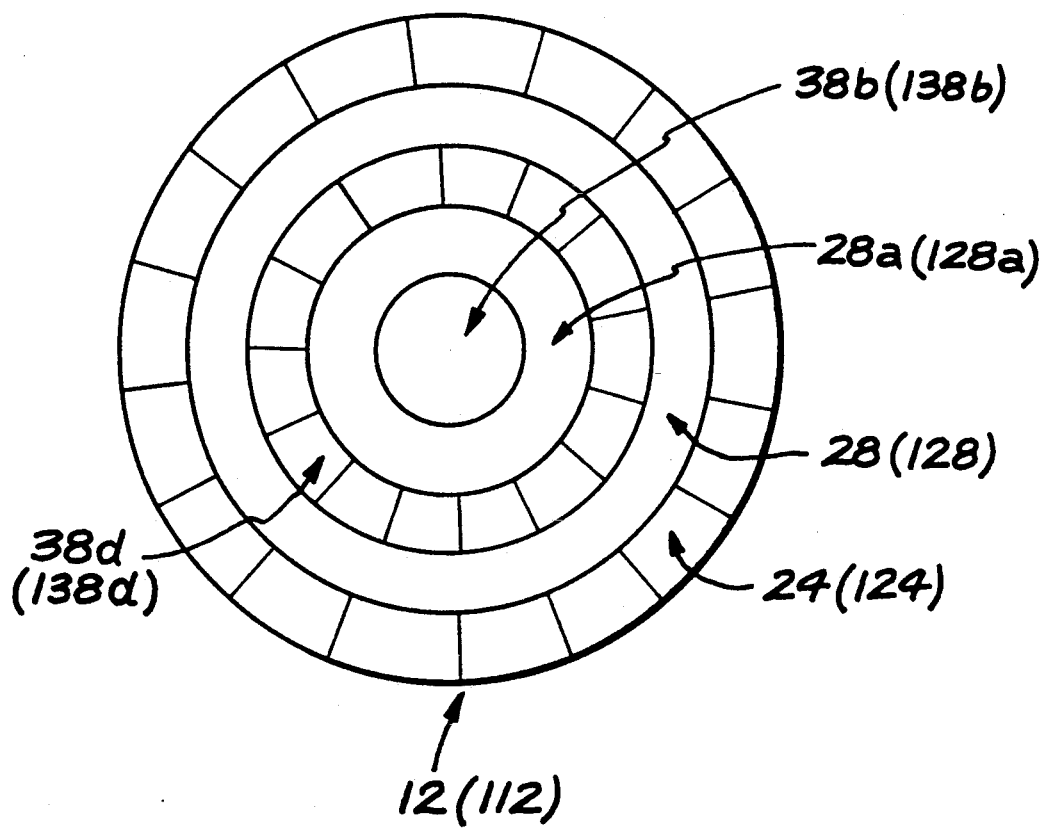

1

INTEGRAL CAP FOR ELECTRODE AND ELECTRODE EMPLOYING SAME

This application is related to copending application Ser. No. 07/566,296 filed Jul. 30, 1990.

This invention relates to electrodes, particularly silver/silver chloride reference electrodes which consist of materials which do not degrade readily in a neutron flux and are therefore suitable for monitoring the coolant within a nuclear reactor.

BACKGROUND OF THE INVENTION

The nuclear power industry long has been engaged in a multitude of studies and investigations seeking improvement in the stamina and reliability of the materials and components forming a reactor-based power system. One such investigation has been concerned with intergranular stress corrosion cracking which heretofore principally has been manifested in the water recirculation piping systems external to the radiation intense reactor core regions of nuclear facilities. Typically, the piping architecture of these external systems is formed of a stainless steel material.

Generally, the studies referred to above have determined that three factors must occur in coincidence to create conditions that promote intergranular stress corrosion cracking. One factor is a sensitization of the metal such as stainless steel, for example, by chromium depletion at grain boundaries. Chromium depletion at grain boundaries may be caused by heat treatment in the course of normal processing of the metal or by welding and like procedures. A second factor is the presence of tensile stress in the material. A third factor is the oxygenated normal water chemistry environment typically present in a boiling water reactor. This latter environment is occasioned by any of a variety of oxidizing and corrosive species contributed by impurities in reactor coolant water. An electrochemical potential monitoring approach has been combined with controlled additions of hydrogen into the coolant to monitor and control the oxygenated environment factor.

Electrochemical potential monitoring is carried out employing paired electrochemical half-cell probes or electrodes which are mounted within the recirculation piping and accessed to the external environment through gland type mountings or the like. Where, as in the instant application, the electrode system of interest involves a metal-metal ion couple, then the reference electrode can conveniently be a metal-metal insoluble salt-anion electrode. A suitable reference electrode may be based, for example, on the half-cell reaction between silver and silver chloride. Calibration of the cell defining electrode pair is carried out by appropriate Nernst based electrochemical calculations, as well as by thermodynamic evaluation in combination with laboratory testing within a simulated environment against a standard electrode.

Half-cell electrodes capable of operation in high pressure and high temperature fluids have been developed for for use in reactor recirculation piping. For example, see U.S. Pat. No. 4,576,667. Such reference electrodes have combined metal housings, ceramic members, and polymeric sealing means formed, for example, from polytetrafluoroethylene or Teflon synthetic resin polymers, to provide electrical isolation of a silver electrode within the reference electrode. These structures have performed adequately in the more benign and essentially radiation free environments of, for example, recirculation piping in nuclear reactors.

Over the recent past, investigators have sought to expand the reference electrode monitoring procedures to the severe environment of the fluid in the vicinity of the reactor core itself for the purpose of studying and quantifying the effect of corrosive species on stress corrosion cracking. Within the reactor core, reference electrodes can be mounted in specially designed small cross section tubing. Such tubing is located among the fuel elements in the reactor core, and is used to house various monitoring devices, such as neutron detectors. As a result, these tubes are known as local power-range monitor tubes.

Thus, the reference electrodes are located in the severe environment of the fluid in the reactor core having a typical high temperature of 274° C., pressure of 1,000 psi, and radiation of $10^9$ rads per hour gamma and $10^{13}$ rads per hour neutron. Reference electrode structures of earlier designs are completely inadequate for this reactor core environment, both from a material standpoint, and with respect to the critical need to prevent leakage of radio-active materials to the ambient environment of the reactor. For example, the polymeric seals used in reference electrodes cannot withstand intense radiation with the result being failure of the electrode and leakage of radioactive materials. In known reference electrodes, leakage at the polymeric seal can cause failure due to electrical shorting between a lead wire within the electrode, and the test environment, i.e., the reactor coolant. An electrode which does not suffer from these deficiencies of prior electrodes would therefore be desirable.

SUMMARY OF THE INVENTION

The present invention provides a reference electrode which has a structure particularly suited for employment within the rigorous environment of the reactor core of a nuclear power facility. The reference electrode is configured so that the ambient pressure of the coolant acts upon the container structure of the electrode to reduce tensile stress at a brazed seal between ceramic members, thereby imparting improved reliability to reference electrodes of this invention. Furthermore, an electrode of this invention is configured so that all members are attached or sealed together as one unit so that external sealing means, such as a metal wire are not required, thereby further improving its reliability. Electrodes of this invention are able to withstand high intensity nuclear radiation and high pressure reactor water as well as elevated temperatures.

The present invention thus provides an electrode comprising a generally cylindrical container of an insulator, said container having a base region with an externally disposed surface attachment region and a first sidewall means extending to a first access opening therefrom for defining a first internally disposed cavity. Means defining a selectively shaped cut-out in said base region that generally extends through said base region. An insert of an insulator positioned within and narrower than said first cavity, said insert having a first selectively shaped base to mate with the selectively shaped cut-out. A cylindrical neck rising from and narrower than said first base, said neck rising to and extending beyond a second base. A second sidewall means extends from said second base, to a second access opening, the second access being at a height less than said first access opening. The second sidewall means extending to said second access opening therefrom defining a second internally disposed cavity with said neck being concentrically disposed within and rising above said second cavity.

The cut-out of the container and first base of the insert being metallized for acceptance of a silver braze. The insert is set in mating relationship with said cut-out by a silver braze, and a silver-salt electrochemical reactant is located within said second cavity. The silver braze and the silver salt forming the half cell reference potential. A generally cylindrical cap means of an insulator is positioned over the first access opening and has means defining a cylindrical cut-out in mating relationship with and brazed to the neck of said insert. The cylindrical cut-out and neck portion mating with said cut-out preferably being metallized for acceptance of said braze. The cap having a stop cock fit with said container so that said cap retains the silver-salt electrochemical reactant within the container while permitting electrolytic communication with the environment outside said first cavity.

Sleeve means formed of a first select metal exhibiting a coefficient of expansion compatible with said insulator of said container and having an acceptance portion for being intimately sealed thereat by brazed connection with said container surface attachment region and having an internal channel extending along the lengthwise extent thereof. The acceptance portion and surface attachment region preferably having a metallized coating for acceptance of the braze. A lead connected in electrical contact with the first base of said insert and insulatively extending therefrom through said internal channel, and positioning and signal transfer means for operatively supporting said sleeve means and conveying electrical signals from said lead.

The first base of the insert and the cut-out of the container can be cylindrical, and preferably, generally conical in shape.

The present invention also provides a container for electrochemical reactants for an electrode comprising, a general cylindrical member of an insulator, said member having a base region with an externally disposed surface attachment region and first sidewall means extending to a first access opening therefrom for defining a first internally disposed cavity, means defining a selectively shaped cut-out in said base region generally extending through said base region. An insert of an insulator positioned within and narrower than said first cavity, said insert having a first selectively shaped base to mate with the selectively shaped cut-out. A cylindrical neck rising from and narrower than said first base, said neck rising to and extending beyond a second base from which second sidewall means extend to a second access opening therefrom which is a height less than said first access opening. The second sidewall means extending to said second access opening defining a second internally disposed cavity with said neck being concentrically disposed within and rising above said second cavity. The cut-out and first base being metallized for acceptance of a silver braze. The insert being set in mating relationship with said cut-out by silver brazing. Generally cylindrical cap means of an insulator is positioned over the first access opening and has means defining a cylindrical cut-out in mating relationship with and brazed to the neck of said insert, said cap having a stop cock fit with said container so that the cap retains the silver-salt electrochemical reactant within the container while permitting electrolytic communication with environment outside said first cavity.

The cut-out of the member and the first base of the insert can be cylindrical, or preferably conical in shape.

The container or member, insert, and cap in this invention are preferably alumina, and most preferably sapphire. The silver-salt in this invention is preferably silver chloride. Other preferred components of the invention will appear hereinafter.

After positioning in a nuclear reactor, ambient pressure from coolant surrounding the reference electrode applies pressure to the conical insert pressing the insert against the mating conical cut-out so that the braze therebetween is a compressed sealing braze that provides added life to the electrode. Thermal expansion differences between the silver braze and the ceramic insert result in tensile stresses that cause silver brazes to lose adherence to ceramic surfaces. However, the compressive force acting upon the braze helps to offset the tensile force and retains the integrity of the seal.

Other objects of the invention will, in part, be obvious and will, in part, appear hereinafter.

The invention, accordingly, comprises the apparatus possessing the construction, combination of elements, and arrangement of parts which are exemplified in the following detailed disclosure. For a fuller understanding of the nature and objects of the invention, reference should be made to the following detailed description taken in connection with the accompanying drawings.

BRIEF DESCRIPTION OF THE DRAWINGS

FIGS. 1 and 2 are each a sectional view of an electrode according to the invention;

FIGS. 3 and 4 are each an enlarged sectional view of a portion of the electrode of FIGS. 1 and 2, respectively.

FIG. 5 shows an overview of a container of the invention without the cap.

DETAILED DESCRIPTION OF THE INVENTION

While having utility in a broad variety of industrial monitoring functions, the electrode structure of the instant invention finds particular utility operating in the rigorous environment of the reactor core of a nuclear power facility. No elastomeric seals or polymeric components are present in its structure. Rather, a brazed and welded assembly consisting only of ceramic and metal parts forms the structure of the device. The metal and ceramic parts are designed in a manner to be brazed together so that the brazed connections provide a reliable seal from the high pressure and high temperature coolant. Such brazed connections are used to replace the polymeric seals used in known reference electrodes.

We have found that not all brazed connections between ceramic members, or metal and ceramic members, provide a reliable seal from the high pressure and high temperature coolant in a nuclear reactor. For example, one problem to be overcome with a brazed connection between a silver electrode and a ceramic member, to provide electrical isolation of the silver electrode, is the thermal expansion miss match of the braze material on the ceramic. The thermal expansion difference between the braze material and the ceramic material causes tensile forces to develop in the braze material so that the braze delaminates from the ceramic and the high pressure and high temperature coolant passes through the brazed connection and shorts out the electrode.

The electrode of this invention finds preferable employment as a reference component of an electrode system involving a metal-metal ion couple and thus the instant electrode can conveniently be a metal insoluble salt-anion electrode, for example, silver salts such as silver bromide, silver iodide, and preferably silver chloride. For the embodiment shown, the device is a silver-silver chloride reference which functions reversibly. In general, these electrodes consist of a silver metal with silver chloride immersed in a solution containing chloride anions. The electrode reaction is:

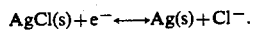

$$AgCl(s) + e^- \longleftrightarrow Ag(s) + Cl^-.$$

At 25° C. the collector electrical potential of such an electrode can be computed as: $V = 0.2222 - 0.05915 \log_{10} a_{Cl^-}$.

For a more detailed discussion in connection with the above, reference is made to "Physical Chemistry" by G. W. Castellan, Chapter 17, "Equilibria in Electrochemical Cells", pp. 344–382, Addision-Wesley Publishing Co., Reading, Mass. (1964).

Referring to FIGS. 1 and 3, the structure of an embodiment of a reference electrode according to the invention is represented in general at 10 in sectional fashion. FIG. 3 shows an enlarged view of the area designated 46 of device 10.

Referring to FIGS. 2 and 4, the structure of another embodiment of a reference electrode according to the invention is represented in general at 110 in sectional fashion. FIG. 4 shows an enlarged view of the area designated 146 in FIG. 2.

Device 10 has a generally cylindrical structure comprised of components including a cylindrically shaped container 12, a generally cylindrical cap 14 inserted into container 12, a sleeve 16 which supports container 12, and an insert 38 positioned in the base of container 12. Insert 38 has a cylindrical base 38a, and has metallization 40 on base 38a. Insert 38 is set in place, at base 38a, by a silver braze 42. Braze 42 is also used as the seal between container 12 and sleeve 16. Rising from base 38a is neck 38b. Neck 38b is also cylindrical and is narrower than base 38a. Neck 38b rises to a base region 38c from which cylindrically shaped wall 38d rises. Neck 38b rises higher than wall 38d. Neck 38b and wall 38d define cavity 28a within which is disposed silver-salt 48. Neck 38b rises to cap 14 and mates therewith as cap 14 is provided with cylindrical cut-out 14a. Braze 42 is also used to seal cap 14 to neck 38b at cut-out 14a. Insert 38, at metallization 40 contacts lead 36 which runs through channel 34 of container 12. Device 10 further comprises an elongate cylindrical transition piece 18 and a cable assembly or connector 20.

The embodiment of FIGS. 2 and 4 differs from that of FIGS. 1 and 3 in that insert 138 of the embodiment of FIGS. 2 and 4 has a conical base 138a rather than a cylindrical one; and, the base 122 of container 112 (FIGS. 2 and 4) accordingly has a conical cut-out 122a. With this distinction set forth, it is noted that structures in FIGS. 2 and 4 which are similar to those of FIGS. 1 and 3 bear reference numbers 100 units greater than those of FIGS. 1 and 3; and same structures among the Figures are numbered the same.

Thus, device 110 has a generally cylindrical structure comprised of components including a cylindrically shaped container 112, a cylindrical cap 14 inserted into container 112, a sleeve 16 which supports container 112, and a conical insert 138 positioned in the base of container 112. Insert 138 has a conical base 138a and metallization 40 on base 138a. Insert 138 is set in place at base 138a by silver braze 42. Braze 42 is also used as the seal between container 112 and sleeve 16. The braze between container 112 and sleeve 16 can be any braze that withstands corrosion from the reactor coolant, and provides a reliable seal. Rising from base 138a is neck 138b. Neck 138b is cylindrical and is narrower than base 138a. Neck 138b rises to a base region 138c from which cylindrically shaped wall 138d rises. Neck 138b and wall 138d define cavity 128a within which is disposed silver-salt 48. Neck 138b rises to cap 14 and mates therewith as cap 14 is provided with cylindrical cut-out 14a. Braze 42 is also used to seal cap 14 to neck 138b at cylindrical cut-out 14a. The braze between cap 14 and neck 138b can be any braze that withstands corrosion from the silver chloride and reactor coolant, and provides a reliable joint. Insert 38, at metallization 40 contacts lead 36 which runs through channel 34 of container 12. Device 110 further comprises an elongate cylindrical transition piece 18 and a cable assembly or connector 20. Silver-salt 48 is within cavity 128a which is within container 112.

Container 12 or 112 is structured not only to withstand the duress otherwise imposed by radiation, high temperatures and pressure, but also to achieve a highly reliable seal to avoid the incursion of reactor coolant water through the electrode and ultimately to the outside environment. Container 12 or 112, insert 38 or 138, and cap 14, are preferably formed of sapphire which is a single crystalline form of alumina. The sapphire material, not only provides a requisite electrical insulation but also, by virtue of its single crystalline structure, is highly resistant to attack by water within which it is immersed. Thus, there is no intergranular penetration into the material even though there will be some general corrosion attack. Accordingly, the material forming container 12 or 112, insert 38 or 138, and cap 14, is ideal for the contemplated environment. Other materials will occur to those art skilled, for example high purity alumina, zirconia, or ruby.

Container 12 or 112 is formed having a cylindrical base region 22 or 122 from which a cylindrically shaped wall 24 or 124 extends to an end surface or access opening 26 into which fits cap 14. The walls 24 or 124 define an internally disposed cavity 28 or 128 within which is disposed insert 38 or 138 and silver-salt 48. Base region 38c or 138c and wall 38d or 138d is not as wide as cavity 28 or 128. Base region 38c or 138c can be about as wide as base 38a or 138a. Cylindrical base region 22 or 122 is formed with channel 34 to accommodate lead 36. Cylindrical base region 22 is also formed with a cylindrical cut-out 22b to accommodate insert 38. Cylindrical base region 122 is formed with a conical cut-out 122b to accommodate insert 138. The cylindrical cut-out 22b or the conical cut-out 122b can be formed by grinding cylindrical base region 22 or 122; and channel 34 can be formed by drilling a hole.

In FIGS. 1–4 conical cut-out 22b and 122b are shown as having channel 34 extending from the cut-out through the base of the container 12 or 112. It is also contemplated that cut-out 22b or 122b can extend through the base of container 12 or 112 so that inset 38 or 138 can extend therethrough. Therefore the selectively shaped cut-out extending through the base region is comprised of cut-outs extending through the base or cut-outs and channels that extend through the base region of container 12 or 112.

To achieve a sealed union of high integrity between base 38a or 138a and cut-out 22b or 122b, a metallized seal of the type known as the sintered metal powder process is made on the ceramic surfaces. A paint containing metal powders such as molybdenum or tungsten, and sometimes containing glass forming or modifying oxides such as $SiO_2$ or MnO is applied to base 38a or 138a and cut-out 22b or 122b and fired in a wet hydrogen atmosphere having dew points in the $-5°$ C. to $+20°$ C. range to sinter the coating. A glassy phase having a mixture of glass and crystalline phases forms a tightly adherent seal on the ceramic insulator. Further explanation of the sintered metal powder process can be found in "Material and Techniques for Electron Tubes" by W. H. Kohl, Reinhold Publishing Corp., N.Y. 1960, pp. 488-493, which is incorporated by reference herein.

The fired surface is inspected and the thus-metallized region is nickel-plated and heated to sinter the metallized layer and nickel plating. The sintered surface is then inspected and silver plated. The inspections are performed to assure the continuity of the platings. Metallization 40 prepares the ceramic surfaces for acceptance of a silver braze bond. The thus-metallized or plated base 38a or 138a are respectively set into the metallized or plated cut-out 22b or 122b of cylindrical base region 22 or 122 of container 12 or 112 by silver braze 42.

Lead 36 may be formed of platinum, iridium or Kovar; Kovar materials are a group of alloys, e.g., Fe 53.8%, Ni 29%, Co 17% and Mn 0.2%, which exhibit a coefficient of thermal expansion characteristic compatible with that of the alumina or other materials suitable for container 12. Lead 36 can be brazed or cemented in electrical contact to metallized insert 38 at point 38e at the end thereof opposite neck 38b (FIG. 3). Lead 36 can also be brazed to metallized insert 138 at the apex or tip thereof at 138e (FIG. 4). Container 12 or 112 is set in place in sleeve 16 by braze 42. Sleeve 16 is also preferably of Kovar.

Shown positioned within cavity 28a (and accordingly cavity 28) or 128a (and accordingly cavity 128) of the retainer or container 12 or 112 is a deposit of silver chloride which herein is shown schematically as a solid dark area at 48. In a preferred arrangement, the silver chloride may be melted and formed into a cylinder which then may be located within cavity 28a or 128a.

End cap 14 is also preferably formed of sapphire, the single crystalline form of alumina and may, for example, be fashioned of the noted alternate materials. Cap 14 is a junction plug. Cylindrical in general form, the cap 14 is seen having a cylindrical cut-out 14a which is brazed to neck 38b or 138b. To facilitate such brazing, the metallization applied to the base 38a and cut-out 22b can be applied to cylindrical cut-out 14a and the portion of neck 38b or 138b mating with the cylindrical cut-out. The cap is dimensioned so as to provide a "tight" or "stop-cock" fit designated 14b over access opening 26 and with the cylindrical interior surface of the cavity 28 or 128. The noted fit of the cap 14 to the container 12 or 112 is one which permits electrolytic communication with the reactor core water. Cap 14 provides a liquid junction which allows for a retention of a supply of silver chloride within cavity 28a or 128a. In effect, a diffusion junction is found between the cap 14 and the wall of the container or retainer or crucible 12 or 112. Exemplary of the type of fit involved, the access opening diameter at container 12 or 112 may, for example, be machined to provide a diameter of 0.235 inch with a tolerance of $+0.001$, $-0.000$, while the corresponding diameter of the neck component 50 at cap 14 may be machined with a diameter of 0.235 inch under tolerances of $+0.00$, $-0.001$ inch. In previous designs, further retention of a cap is by a stainless steel hold-down wire. In the present invention, the hold-down wire is not necessary, however, as the design of the present invention obviates the need for such a hold-down wire as was used in previous devices. Accordingly, the present invention overcomes problems that were inherent in the presence of a hold-down wire, e.g., wire corrosion or breakage causing electrode failure.

Each of container 12 of device 10 and container 112 of device 110 is initially supported by the cylindrical crucible sleeve 16 which, to achieve compatibility with sapphire container 12 or 112 from the standpoint of the thermal coefficient of expansion thereof, is preferably formed also of Kovar. The internal diameter of the sleeve 16 is offset, for example, by counterboring to provide an acceptance portion 58 suited for receiving and being attached to the surface attachment region 22b of base region 22 of container 12 or to the surface attachment region 122b of base region 122 of container 112 for forming an intimate seal thereat. The initially produced cylinder of Kovar for sleeve 16 is prepared by initially cleaning and inspecting it, following which a post machine annealing procedure is carried out. Following this annealing procedure, the acceptance portion 58 is nickel-plated and the nickel-plating is sintered, following which it is inspected. A second nickel-plating and sintering procedure is then carried out, followed by a next inspection. Generally, the thus-prepared component is stored in sealed plastic packaging until it is utilized. An intimate compressive seal of the surface attachment region 22b of container 12 or of the surface attachment region 122b of container 112 with the acceptance portion 58 of sleeve 16 is provided by silver brazing 42. To facilitate such brazing the metallization applied to base 38a can be applied to surface attachment region 22b or 122b. This arrangement then completes a highly secure seal for electrode 10 as is required in view of the intended use thereof within the environment of a nuclear core reactor. The hollow interior 60 of cylindrical (annular) sleeve 16 provides an internal channel through which the conductor lead 36 may pass. To assure that lead 36 is insulated from the internal surfaces of sleeve 16, a tube 62 can be inserted within channel 60. Annular tube 62 can be of ceramic or alumina to provide insulation while remaining immune from the temperatures encountered with the intended use of device 10 or device 110.

Kovar sleeve 16 is supported, in turn, by attachment to the cylindrical transition component 18 which, for the instant application may be formed of a type 304 stainless steel. The transition piece 18 is of corresponding diametric extent as sleeve 16 and is attached at its transition end 64 to the corresponding attachment surface 66 thereof utilizing a tungsten inert gas weld (TIG) as applied, for example, by a tube welder. The hollow interior 68 of transition tube 18 provides an internal channel representing a continuation of the channel 60 of sleeve 16. Tube 62 is seen to extend continuously thereinto. The lower end of the transition tube 18 is formed in necked down fashion to provide a sealing end 70. End 70 is welded, such as by the noted tungsten inert gas welding technique, to the cylindrical stainless steel collar 72 of a cable connector assembly represented generally at 74 and which is shown having a ceramic support component 76 through which a mineral insulated cable 78 extends. Cable 78 may be provided having a stainless steel outer shell within which the noted mineral insulation may be provided as alumina and centrally disposed within which is a conducting cable 80. The mineral insulated cable 78 extends outwardly to the ambient environment from the reactor core region in the application of interest. To provide an electric circuit completing connection with cable 80, lead 36 is spot welded thereto at 82. To facilitate this attachment with the lead 36, a spring winding is formed in lead 36 as represented in general at 84. Cable assembly 74 is marketed, for example, by Reutor-Stokes, a division of General Electric Company, Twinsburg, Ohio. As mentioned earlier, area 46 of FIG. 1 is shown enlarged in FIG. 3 and area 146 of FIG. 2 is shown enlarged in FIG. 4. The design of the present electrode, especially as shown in enlarged detail in FIGS. 2 and 4 benefits from the ambient pressure differential between the coolant in a nuclear reactor core and the inside of the electrode. The conductivity of the braze metal eliminates the requirement for a second metal in the vulnerable inner chamber of the electrode. The conical configuration of insert 38 maintains a uniform ceramic/ceramic gap with vertical displacement of the insert. The optimization of the diameter/depth/contact angle of the insert is within the ambit of the skilled artisan from this disclosure. Ambient pressure from the coolant helps reduce tensile stress at the ceramic/silver interface due to the shape of the insert and the matching cut-out in the base region. The insert is provided with a cavity for holding the silver chloride deposit within the container so that the silver chloride does not affect the integrity of the brazes by coming into contact with the brazed areas during brazing. The integral joining relation of the cap, insert, and container also provides for retention of the cap on the container without the need for an external clamp or holder such as a wire to hold the cap in place. The external Kovar sleeve 16 provides a compressive brazed seal between container 12 and sleeve 16. Reduction of the tensile stress between ceramic members and braze materials, as described above, significantly improves the reliability of reference electrodes of the present invention. Reference electrodes of the present invention are useful for monitoring electrochemical potentials.

With reference to FIGS. 3 and 4, it is to be noted that container 12 or 112 is also labelled "A", insert 38 or 138 is also labelled "B", and that cap 14 is labelled "C". These reference letters are provided for an understanding of the fabrication of these components which proceeds by:

1. Grinding container A, insert B, and cap C from a suitable material such as single crystal sapphire. At least the cut-out at the base of the container and the insert base are metallized for acceptance of a silver braze.
2. Inverting the assembly of B and C, and brazing B and C together using A or an equivalent jig to achieve exact alignment.
3. Filling the annular chamber cavity 28a or 128a with silver chloride.
4. Silver brazing the insert 38 or 138 to the container (12 or 112), and brazing the Kovar sleeve 16 to the container (12 or 112), in the upright position shown in FIGS. 1-4.

The annular chamber cavity 28a or 128a retains the silver chloride which becomes molten during final brazing, and prevents any interference with forming the ceramic/ceramic pressure seal. Water entering the chamber (cavity 28a or 128a) e.g., during use, will dissolve sufficient silver chloride for saturation inside the electrode, and establish a stable reference potential.

FIG. 5 shows an overview of a container of the invention, i.e., looking down upon container 12 or 112 with cap 14 removed and no metal-salt 48 within cavity 28a or 128a. FIG. 5 shows the concentric relationship among wall 24 or 124 (defining cavity 28 or 128), wall 38d or 138d (defining cavity 28a or 128a) neck 38b or 138b.

Having thus described in detail preferred embodiments of the present invention, it is to be understood that the invention defined by the appended claims is not to be limited by particular details set forth in the above description as many apparent variations thereof are possible without departing form the spirit or scope of the present invention.

What is claimed is:

1. An electrode comprising:
    a generally cylindrical container of an insulator, said container having a base region with an externally disposed surface attachment region and first sidewall means extending to a first access opening therefrom for defining a first internally disposed cavity, means defining a selectively shaped cut-out in said base region extending through said base region,
    an insert of an insulator positioned within and narrower than said first cavity, said insert having a first, selectively shaped base to mate with the selectively shaped cut-out, a cylindrical neck rising from and narrower than said first base, said neck rising to and extending beyond a second base from which a second sidewall means extends to a second access opening therefrom which is at a height less than said first access opening, said second sidewall means extending to said second access opening therefrom defining a second internally disposed cavity with said neck being concentrically disposed within and rising above said second cavity, at least said first base and cut-out being metallized for acceptance of a silver braze, said insert being set in mating relationship with said cut-out by a silver braze,
    a silver-salt electromechanical reactant located within said second cavity,
    a generally cylindrical cap means of an insulator positioned over the first access opening and having means defining a cylindrical cut-out in mating relationship with and brazed to the neck of said insert, said cap having a stop cock fit with said container so that said cap retains the silver-salt electrochemical reactant within the container while permitting electrolytic communication with the environment outside said first cavity,
    a sleeve means formed of a select metal exhibiting a coefficient of expansion compatible with said insulator material of said container and having an acceptance portion for and being intimately sealed thereat by brazed connection with said container surface attachment region and having an internal channel extending along the lengthwise extent thereof, a lead connected in electrical contact with the first base of said insert and insulatively extending therefrom through said internal channel, and a positioning and signal transfer means for operatively supporting said sleeve means and conveying electrical signals from said lead.

2. The electrode of claim 1 in which said positioning and signal transfer means comprises:

a transition component formed of a select metal and having an internal channel extending therethrough to a sealing end and sealably connected with said sleeve means, said lead extending into the internal channel of the transition component, and a cable connector means having a collar weldably attached and sealed to said transition component sealing end and having a conductor extending therethrough for connection with the lead.

3. The electrode of claim 2 wherein said transition component is formed of stainless steel and is welded to said sleeve means to form a continuous internal channel from said internal channel of the transition component and the internal channel of said sleeve means.

4. The electrode of claim 3 wherein said sleeve means is comprised of Kovar.

5. The electrode of claim 1 wherein the insulator of said container, insert and cap comprise alumina.

6. The electrode of claim 5 wherein the alumina comprises sapphire.

7. The electrode of claim 1 wherein the sleeve means is comprised of Kovar.

8. The electrode of claim 1 wherein the lead is comprised of platinum.

9. The electrode of claim 1 wherein the silver-salt electrochemical reactant comprises silver chloride.

10. The electrode of claim 1 wherein said first base of said insert and said cut-out of said container are generally conical in shape.

11. The electrode of claim 1 wherein said first base of said insert and said cut-out of said container are generally cylindrical in shape.

12. A container including cap for electrochemical reactants for an electrode and comprising a generally cylindrical member of an insulator, said member having a base region with an externally disposed surface attachment region and first sidewall means extending to a first access opening therefrom for defining a first internally disposed cavity, means defining a selectively shaped cut-out in said base region extending through said base region, an insert of an insulator positioned within and narrower than said first cavity, said insert having a first selectively shaped base to mate with the selectively shaped cut-out, a cylindrical neck rising from and narrower than said first base, said neck rising to and extending beyond a second base from which second sidewall means extend to a second access opening therefrom which is at a height less than said first access opening, said second sidewall means extending to said second access opening therefrom to define a second internally disposed cavity with said neck being concentrically disposed within and rising above said second cavity, at least said first base and cut-out being metallized for acceptance of a silver braze, said insert being set in mating relationship with said cut-out by a silver braze, and generally cylindrical cap means of an insulator positioned over the first access opening and having means defining a cylindrical cut-out in mating relationship with and brazed to the neck of said insert, said cap having a stop cock fit with said member so that said cap retains a metal-salt electrochemical reactant within the member while permitting electrolytic communication with environment outside said first cavity.

13. The container of claim 12 wherein the insulator of said member and of said insert and of said cap comprises alumina.

14. The container of claim 13 wherein the alumina comprises sapphire.

15. The container of claim 12 wherein the cut-out and the first base of said insert are conical in shape.

16. The container of the claim 12 wherein the cut-out and the first base of said insert are cylindrical in shape.

17. A reference electrode for employment within a fluid media and having an electrode system involving a metal/metal ion couple, comprising:

a generally cylindrical container of alumina, said container having a base region with an externally disposed surface attachment region and first sidewall means extending to a first access opening therefrom for defining a first internally disposed cavity, means defining a selectively shaped cut-out in said base region extending through said base region, an insert of alumina positioned within and narrower than said first cavity, said insert having a first selectively shaped base to mate with the selectively shaped cut-out, a cylindrical neck rising from and narrower than said first base, said neck rising to and e tending beyond a second base from which second sidewall means extend to a second access opening therefrom which is at a height less than said first access opening, said second sidewall means extending to said second access opening therefrom define a second internally disposed cavity with said neck being concentrically disposed within and rising above said second cavity, at least said first base and cut-out being metallized for acceptance of a silver braze, said insert being set in mating relationship with said cut-out by a silver braze, a silver-chloride electrochemical reactant located within said second cavity, a generally cylindrical cap means of alumina positioned over the first access opening and having means defining a cylindrical cut-out in mating relationship with and brazed to the neck of said insert, said cap having a stop cock fit with said container so that said cap retains the silver chloride electrochemical reactant within the container while permitting electrolytic communication with said fluid media, a sleeve means formed of Kovar having an acceptance portion for and being intimately sealed thereat by silver brazed connection with said container surface attachment region and having a first internal channel extending along the lengthwise extent thereof, a platinum lead connected in electrical contact with the first base of said insert and insulatively extending therefrom through said internal channel.

a transition component formed of stainless steel having a second internal channel extending therethrough to a sealing end, the transition component being sealably connected with said sleeve means, said lead extending into the internal channel of the transition component, and cable connector means having a collar weldably attached and sealed to said transition component sealing end and having a conductor extending therethrough for connection with the lead.

18. The reference electrode of claim 17 wherein the member, insert, and cap are comprised of sapphire.

19. The reference electrode of claim 17 including an alumina tube located within said first and second channels through which said conductor extends for effecting the insulation thereof.

20. The reference electrode of claim 17 in which said alumina container externally disposed surface attachment region is nestably positioned within said sleeve means acceptance portion and is sealed thereto with a silver braze.

21. The reference electrode of claim 17 in which said outer surface of said generally conical insert is metallized by providing a sequence of coatings including a fired, metallized surface coating which is covered with a sintered nickel plate, over which is formed a silver plate.

22. The reference electrode of claim 17 in which said acceptance portion is coated with a sintered nickel plate coating.

23. The reference electrode of claim 17 wherein said cut-out of said container and said first base of said insert are conical in shape.

24. The reference electrode of claim 17 wherein said cut-out of said container and said first base of said insert are cylindrical in shape.

* * * * *